(12) United States Patent
Lee (10) Patent No.: US 10,034,811 B2
(45) Date of Patent: Jul. 31, 2018

(54) METHOD AND APPARATUS FOR CALCULATING ASSISTANCE TORQUES

(71) Applicant: Samsung Electronics Co., Ltd., Suwon-si, Gyeonggi-do (KR)

(72) Inventor: Jusuk Lee, Hwaseong-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 131 days.

(21) Appl. No.: 14/988,382

(22) Filed: Jan. 5, 2016

(65) Prior Publication Data

US 2017/0056274 A1  Mar. 2, 2017

(30) Foreign Application Priority Data

Aug. 28, 2015 (KR) .................. 10-2015-0121886

(51) Int. Cl.
| | |
|---|---|
| *A61F 2/70* | (2006.01) |
| *A61H 3/00* | (2006.01) |
| *B25J 13/08* | (2006.01) |

(Continued)

(52) U.S. Cl.
CPC ............ *A61H 3/00* (2013.01); *A61F 2/70* (2013.01); *A61F 5/0102* (2013.01);
(Continued)

(58) Field of Classification Search
CPC ........ B25J 9/0006; B25J 9/126; B25J 13/085; B25J 13/088; G05B 2219/40305
See application file for complete search history.

(56) References Cited

U.S. PATENT DOCUMENTS

| | | | |
|---|---|---|---|
| 2007/0123997 A1 | 5/2007 | Herr et al. | |
| 2008/0161937 A1* | 7/2008 | Sankai | A61H 3/008 623/25 |

(Continued)

FOREIGN PATENT DOCUMENTS

| | | |
|---|---|---|
| JP | 4345025 B2 | 10/2009 |
| JP | 4559612 B2 | 10/2010 |

(Continued)

OTHER PUBLICATIONS

F. Giovacchini, et al., "A light-weight active orthosis for hip movement assistance", Robotics and Autonomous System, 2014.

*Primary Examiner* — Dale Moyer
(74) *Attorney, Agent, or Firm* — Harness, Dickey & Pierce, P.L.C.

(57) ABSTRACT

A method may include: calculating a first assistance torque to be provided to a user wearing a walking assistance apparatus; measuring a degree of twisting of a portion of the apparatus; calculating a second assistance torque transferred to the user based on the degree of twisting; and/or calculating a third assistance torque based on the first and second assistance torques, the third assistance torque corresponding to correction of the twisting. An assistance torque calculation apparatus may include: a bend sensor configured to measure a degree of twisting of a portion of a walking assistance apparatus; and/or a processor configured to calculate a first assistance torque to be provided to a user wearing the walking assistance apparatus, configured to calculate a second assistance torque transferred to the user based on the degree of twisting, and/or configured to calculate a third assistance torque based on the first and second assistance torques.

17 Claims, 9 Drawing Sheets

(51) Int. Cl.
*A61H 1/02* (2006.01)
*B25J 9/12* (2006.01)
*B25J 9/00* (2006.01)
*A61F 5/01* (2006.01)

(52) U.S. Cl.
CPC ......... *A61H 1/0244* (2013.01); *B25J 9/0006* (2013.01); *B25J 9/126* (2013.01); *B25J 13/085* (2013.01); *B25J 13/088* (2013.01); *A61F 2005/0155* (2013.01); *A61F 2250/0074* (2013.01); *A61H 2201/0165* (2013.01); *A61H 2201/1215* (2013.01); *A61H 2201/164* (2013.01); *A61H 2201/165* (2013.01); *A61H 2201/5005* (2013.01); *A61H 2201/5007* (2013.01); *A61H 2201/5048* (2013.01); *A61H 2201/5058* (2013.01); *A61H 2201/5061* (2013.01); *A61H 2201/5069* (2013.01); *A61H 2201/5071* (2013.01); *A61H 2201/5079* (2013.01); *A61H 2201/5084* (2013.01); *A61H 2201/5097* (2013.01); *A61H 2230/605* (2013.01)

(56) References Cited

U.S. PATENT DOCUMENTS

| | | | | |
|---|---|---|---|---|
| 2010/0113980 | A1* | 5/2010 | Herr | A61F 2/60 600/587 |
| 2011/0164949 | A1* | 7/2011 | Kim | B25J 9/0006 414/1 |
| 2012/0330198 | A1 | 12/2012 | Patoglu | |
| 2014/0221894 | A1* | 8/2014 | Nagasaka | A61H 3/00 602/23 |
| 2015/0134080 | A1* | 5/2015 | Roh | B25J 9/0006 623/32 |

FOREIGN PATENT DOCUMENTS

| | | |
|---|---|---|
| JP | 2014068873 A | 4/2014 |
| KR | 100598504 B1 | 7/2006 |
| KR | 10-0869264 B1 | 11/2008 |
| KR | 101317354 B1 | 10/2013 |
| KR | 101350334 B1 | 1/2014 |

* cited by examiner

METHOD AND APPARATUS FOR CALCULATING ASSISTANCE TORQUES

CROSS-REFERENCE TO RELATED APPLICATION(S)

This application claims priority from Korean Patent Application No. 10-2015-0121886, filed on Aug. 28, 2015, in the Korean Intellectual Property Office (KIPO), the entire contents of which are incorporated herein by reference.

BACKGROUND

1. Field

At least one example embodiment may relate generally to methods for calculating assistance torques. At least one example embodiment may relate generally to apparatuses for calculating assistance torques. At least one example embodiment may relate generally to methods for calculating assistance torques provided by walking assistance apparatuses. At least one example embodiment may relate generally to apparatuses for calculating assistance torques provided by walking assistance apparatuses.

2. Description of Related Art

With the onset of rapidly aging societies, many people may experience inconvenience and/or pain from joint problems. Thus, there may be growing interest in walking assistance apparatuses that may enable the elderly and/or patients having joint problems to walk with less effort. Furthermore, walking assistance apparatuses for intensifying muscular strength of human bodies may be useful for military purposes.

The users may wear the walking assistance apparatuses over the users' clothing.

Although some example embodiments will be described with relation to walking assistance methods and walking assistance apparatuses for humans, those skilled in the art will appreciate that some example embodiments may be applied to other types of methods, apparatuses, and systems, such as motion assistance methods and motion assistance apparatuses for animals, or more general purpose systems.

SUMMARY

Some example embodiments may provide assistance torque calculation methods.

Some example embodiments may provide assistance torque calculation apparatuses.

In some example embodiments, an assistance torque calculation method may comprise: calculating a first assistance torque to be provided to a user wearing a walking assistance apparatus; measuring a degree of twisting of a portion of the walking assistance apparatus; calculating a second assistance torque transferred to the user based on the degree of twisting; and/or calculating a third assistance torque based on the first assistance torque and the second assistance torque, the third assistance torque corresponding to correction of the twisting.

In some example embodiments, the measuring of the degree of twisting may comprise measuring the degree of twisting using a bend sensor attached to the portion of the walking assistance apparatus.

In some example embodiments, the bend sensor may comprise a flex sensor.

In some example embodiments, the bend sensor may comprise an optical fiber Bragg grating sensor.

In some example embodiments, the calculating of the third assistance torque may comprise calculating a difference between the first assistance torque and the second assistance torque as the third assistance torque.

In some example embodiments, the assistance torque calculation method may further comprise: controlling the walking assistance apparatus to output the third assistance torque.

In some example embodiments, the controlling of the walking assistance apparatus may comprise: calculating a current value to generate the third assistance torque, based on a motor constant; and/or outputting the third assistance torque by driving a motor based on the current value.

In some example embodiments, the calculating of the second assistance torque may comprise calculating the second assistance torque using a transformation function.

In some example embodiments, the assistance torque calculation method may further comprise: generating the transformation function, prior to the calculating of the first assistance torque. The transformation function may be used to match the degree of twisting to the second assistance torque.

In some example embodiments, the generating of the transformation function may comprise: controlling a motor to output a test assistance torque; receiving information about a pressure generated in a part of a body of the user by the test assistance torque; calculating an applied assistance torque based on the pressure; measuring the degree of twisting of the portion of the walking assistance apparatus twisted by the test assistance torque; and/or generating the transformation function based on the degree of twisting and the applied assistance torque.

In some example embodiments, the information about the pressure may be generated by a pressure sensor.

In some example embodiments, the part of the body may be a thigh.

In some example embodiments, the calculating of the first assistance torque may comprise calculating the first assistance torque based on an operating state of the walking assistance apparatus.

In some example embodiments, the operating state may be determined based on movement of the user.

In some example embodiments, the portion may be a portion supporting a waist of the user.

In some example embodiments, an assistance torque calculation apparatus may comprise: a bend sensor configured to measure a degree of twisting of a portion of a walking assistance apparatus; and/or a processor configured to calculate a first assistance torque to be provided to a user wearing the walking assistance apparatus, configured to calculate a second assistance torque transferred to the user based on the degree of twisting, and/or configured to calculate a third assistance torque based on the first assistance torque and the second assistance torque, the third assistance torque corresponding to correction of the twisting.

In some example embodiments, the bend sensor may comprise a flex sensor.

In some example embodiments, the bend sensor may comprise an optical fiber Bragg grating sensor.

In some example embodiments, the processor may be further configured to calculate the second assistance torque using a transformation function.

In some example embodiments, the processor may be further configured to control a driving portion of the walking assistance apparatus to output a test assistance torque, configured to receive information about a pressure generated in a part of a body of the user by the test assistance torque, and/or configured to calculate an applied assistance torque based on the pressure. The bend sensor may be further configured to measure the degree of twisting of the portion of the walking assistance apparatus twisted by the test assistance torque. The processor may be further configured to generate the transformation function based on the degree of twisting and the applied assistance torque.

In some example embodiments, the part of the body may be a thigh.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

<Summary of Walking Assistance Apparatus>

Figure 1:
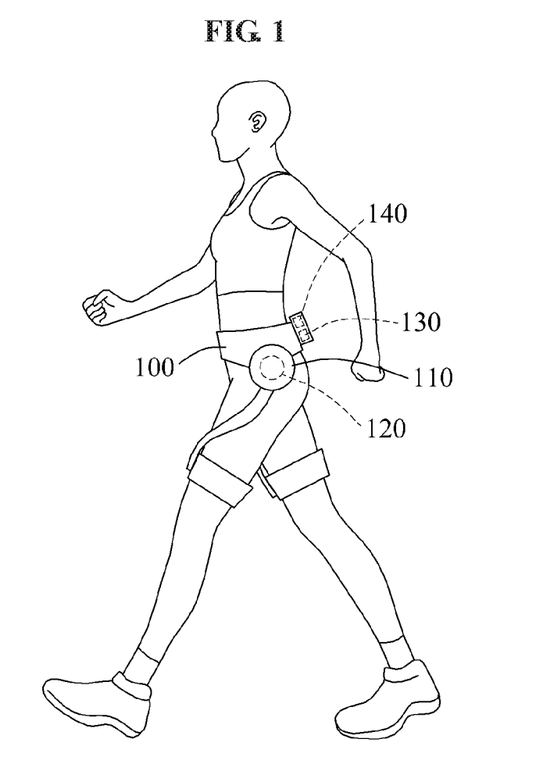
FIGS. 1 and 2 illustrate a walking assistance apparatus according to at least one example embodiment.
Figure 2:
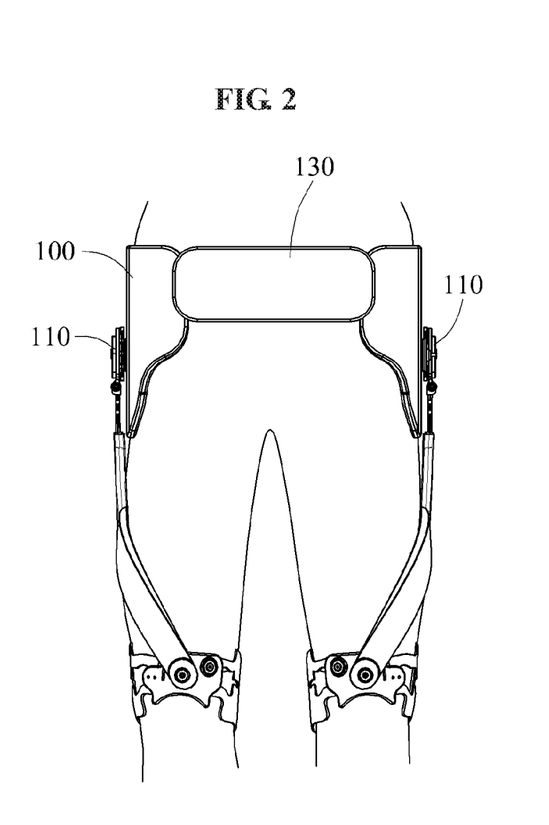

FIGS. 1 and 2 illustrate a walking assistance apparatus 100 according to at least one example embodiment.

Referring to FIG. 1, the walking assistance apparatus 100 may be worn on a user and may assist walking of the user. The walking assistance apparatus 100 may be a wearable device.

FIG. 1 illustrates an example of a hip-type walking assistance apparatus, however, a type of walking assistance apparatuses is not limited to the hip-type walking assistance apparatus. Accordingly, the walking assistance apparatus 100 may be, for example, a walking assistance apparatus for supporting an entire pelvic limb or a walking assistance apparatus for supporting a portion of a pelvic limb. Also, the walking assistance apparatus 100 may be, for example, one of a walking assistance apparatus for supporting a portion of a pelvic limb, a walking assistance apparatus for supporting up to a knee, and a walking assistance apparatus for supporting up to an ankle, or a walking assistance apparatus for supporting a whole body.

Example embodiments described with reference to FIG. 1 and the like may be applicable to a hip-type walking assistance apparatus, however, there is no limitation thereto. Accordingly, example embodiments may be applicable to any type of apparatuses for assisting walking of a user.

In some example embodiments, a walking assistance apparatus for a robot could establish a master/slave or slave/master relationship between the walking assistance apparatus and robot. Such a master device may not be a single device, but may include more than one device, each performing one or more functions of the master device (e.g., the functionality of the master device may be distributed). Similarly, the slave device may not be a single device, but may include more than one device, each performing one or more functions of the slave device (e.g., the functionality of the slave device may be distributed). Therefore, the functionality of the master device, the slave device, or the master and slave devices may be distributed.

In some example embodiments, in such master/slave or slave/master relationship, the master device may be required to perform certain functions, but may or may not perform other functions while maintaining its role as the master device. One or more of these other functions may be shared with or performed by the slave device (which maintains its role as the slave device). Similarly, the slave device may be required to perform certain functions, but may or may not perform other functions while maintaining its role as the slave device. One or more of those other functions may be shared with or performed by the master device (which maintains its role as the master device). Thus, the required functionality of the master and slave devices may be maintained, while functionality that may be shared with or performed by the other device may be so shared with or performed by the other device consistent with the master device maintaining its role as the master device and the slave device maintaining its role as the slave device.

Although FIG. 2 illustrates a case in which the walking assistance apparatus 100 is a two-sided embodiment, in some example embodiments, the walking assistance apparatus 100 may be a one-sided embodiment.

Although FIG. 2 illustrates a case in which the walking assistance apparatus 100 may assist a motion of both thighs of the user, in some example embodiments, the walking assistance apparatus 100 may also assist a motion of only one thigh of a user at a time.

Referring to FIG. 1, the walking assistance apparatus 100 may include a driving portion 110, a sensor 120, an inertial measurement unit (IMU) sensor 130, and a controller 140.

The driving portion 110 may drive both hip joints of a user. The driving portion 110 may be located on, for example, a right hip portion and/or a left hip portion of the user.

For example, the driving portion 110 may include a motor to generate a rotational torque. The driving portion 110 may generate a rotational torque and generate an assistance torque to move legs based on the rotational torque. The assistance torque may be used to generate an assistance force to be provided to legs. The assistance force may be generated in proportional to the assistance torque, and accordingly the terms "assistance force" and "assistance torque" may be used interchangeably with respect to each other.

The sensor 120 may measure hip joint angles of the hip joints of the user while the user is ambulatory. Information about the hip joint angles sensed by the sensor 120 may include, for example, an angle of a right hip joint, an angle of a left hip joint, a difference between both the hip joint angles, or a direction of motion for a hip joint. The sensor 120 may be located in, for example, the driving portion 110.

The sensor 120 may include a potentiometer. The potentiometer may sense a right (R)-axis joint angle, a left (L)-axis joint angle, an R-axis joint angular velocity, and an L-axis joint angular velocity, based on a gait motion of the user.

The IMU sensor 130 may measure acceleration information and posture information while the user is ambulatory. For example, the IMU sensor 130 may sense an x-axis acceleration, a y-axis acceleration, a z-axis acceleration, an x-axis angular velocity, a y-axis angular velocity, and a z-axis angular velocity, based on a gait motion of the user.

The walking assistance apparatus 100 may detect a point at which a foot of the user lands based on the acceleration information measured by the IMU sensor 130.

A pressure sensor (not shown) may be attached to a sole of the user, and may detect a point in time at which a foot of the user lands.

The walking assistance apparatus 100 may include, in addition to the above-described sensor 120 and IMU sensor 130, another sensor (for example, an electromyography (EMG) sensor) configured to sense a change in a biosignal or a quantity of motion of a user based on a gait motion.

The controller 140 may control the driving portion 110 to output an assistance torque to assist walking of the user. Because the walking assistance apparatus 100 is a hip-type walking assistance apparatus, two driving portions 110 may be provided for a left hip portion and a right hip portion, and the controller 140 may output a control signal to control the driving portions 110 to generate torques.

The driving portions 110 may generate torques based on the control signal output from the controller 140.

The torques may be set by the controller 140 or by an external device connected via a wired or wireless network.

The walking assistance apparatus 100 may include a driving portion 110 for a right leg and a driving portion 110 for a left leg.

In an example, the controller 140 may be designed to control one of the driving portions 110. In this example, a plurality of controllers 140 may be provided.

In another example, the controller 140 may be designed to control both the driving portions 110.

Figure 3:
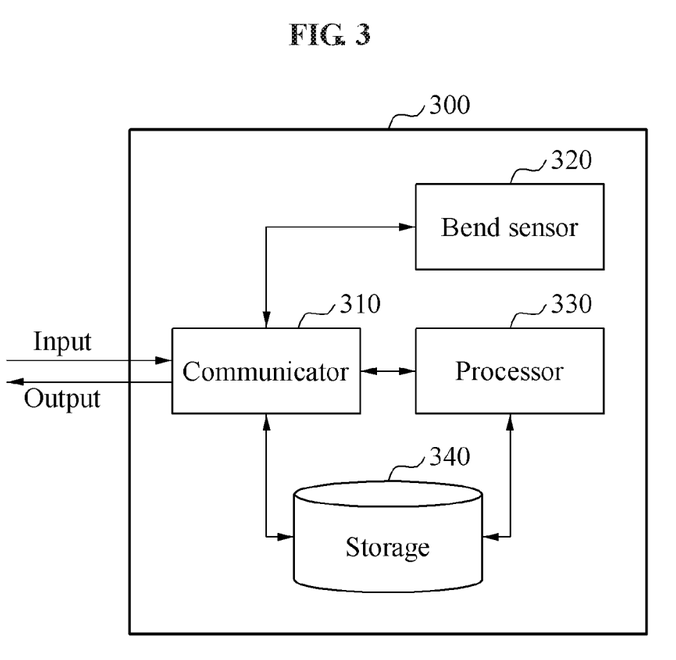
FIG. 3 illustrates a configuration of an assistance torque calculation apparatus according to at least one example embodiment.

FIG. 3 illustrates a configuration of an assistance torque calculation apparatus 300 according to at least one example embodiment.

The assistance torque calculation apparatus 300 (hereinafter, referred to as a controller 300) may include a communicator 310, a bend sensor 320, a processor 330, and a storage 340. The controller 300 may correspond to the above-described controller 140.

The communicator 310 may exchange data with the bend sensor 320, the processor 330, and the storage 340, and may communicate with other devices.

The processor 330 may process data received by the communicator 310 and data stored in the storage 340.

The storage 340 may store the data received by the communicator 310 and data processed by the processor 330.

The communicator 310, the bend sensor 320, the processor 330, and the storage 340 will be further described with reference to FIGS. 4, 5, 6, 7, 8 and 9.

<Assistance Torque Calculation Method of Walking Assistance Apparatus>

Figure 8:
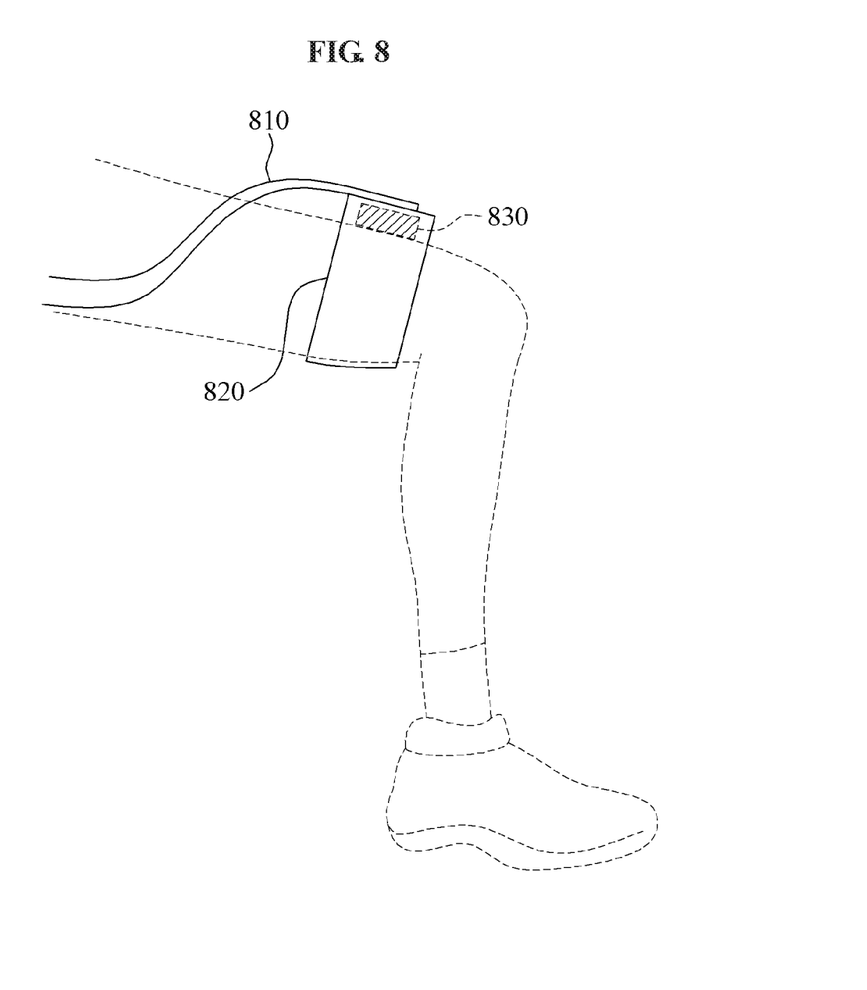
FIG. 8 illustrates an example of a position in which a pressure sensor is attached according to at least one example embodiment.
Figure 9:
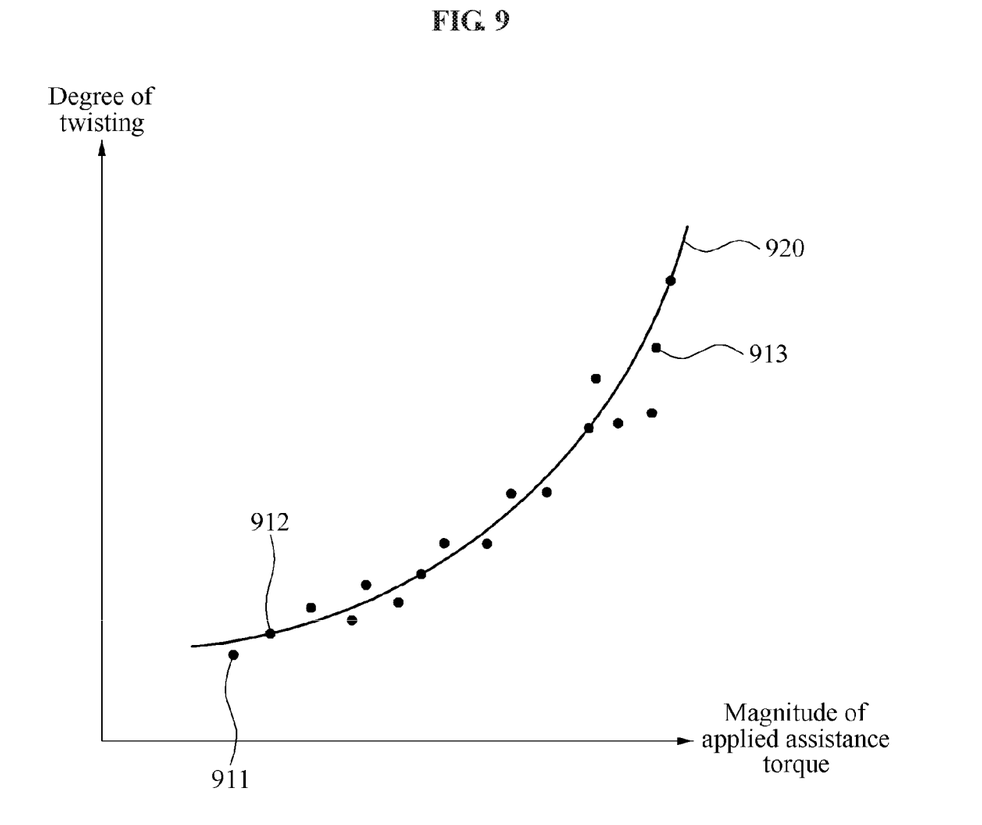
FIG. 9 illustrates a graph of a transformation function according to at least one example embodiment.
Figure 10:
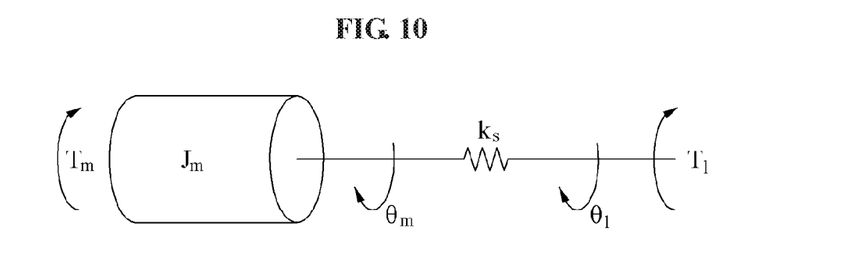
FIG. 10 illustrates an example of modeling a torque sensor according to at least one example embodiment.

Description of FIG. 10 is provided prior to description of FIGS. 4 through 9.

FIG. 10 illustrates an example of modeling a torque sensor according to at least one example embodiment.

The torque sensor may be located between a portion to generate a torque and a portion to receive a torque, to measure a torque to be transferred to a user. The torque sensor may be, for example, a serial elastic actuator (SEA).

The SEA may include a mass and a spring. In FIG. 10, $J_m$ denotes a mass, $k_s$ denotes a spring constant, $T_m$ denotes an input torque, and $T_l$ denotes an output torque.

Angles $\theta_m$ and $\theta_l$ of both sides of the spring may be measured using two encoders. The output torque $T_l$ may be calculated based on the spring constant $k_s$ and a difference between the angles $\theta_m$ and $\theta_l$.

In an example, using the SEA, it is possible to obtain an effect of reducing a strong torque unexpectedly generated in an input terminal (for example, a motor) using a spring located in a central portion of the SEA and of transferring the torque to an output terminal, which is referred to an inherent compliance.

In another example, using the SEA, a shock unexpectedly generated in the output terminal may be absorbed by the spring located in the central portion of the SEA. When the shock is absorbed by the spring, a shock applied to the input terminal may be reduced. By reducing the shock applied to the input terminal, a degradation in the input terminal may be prevented, which is referred to as a shock tolerance.

An effect similar to the SEA may be obtained using a support frame of the walking assistance apparatus 100. The support frame of the walking assistance apparatus 100 may correspond to, for example, the spring of the SEA. When the support frame is formed of a deformable material (for example, a carbon fiber), the support frame may perform a function of the spring of the SEA.

When the support frame performs the function of the spring of the SEA, an assistance torque needing to be transferred may be reduced by the support frame. A scheme of calculating an output assistance torque based on an assistance torque reduced by the support frame will be further described with reference to FIGS. 4 through 9 below.

Figure 4:
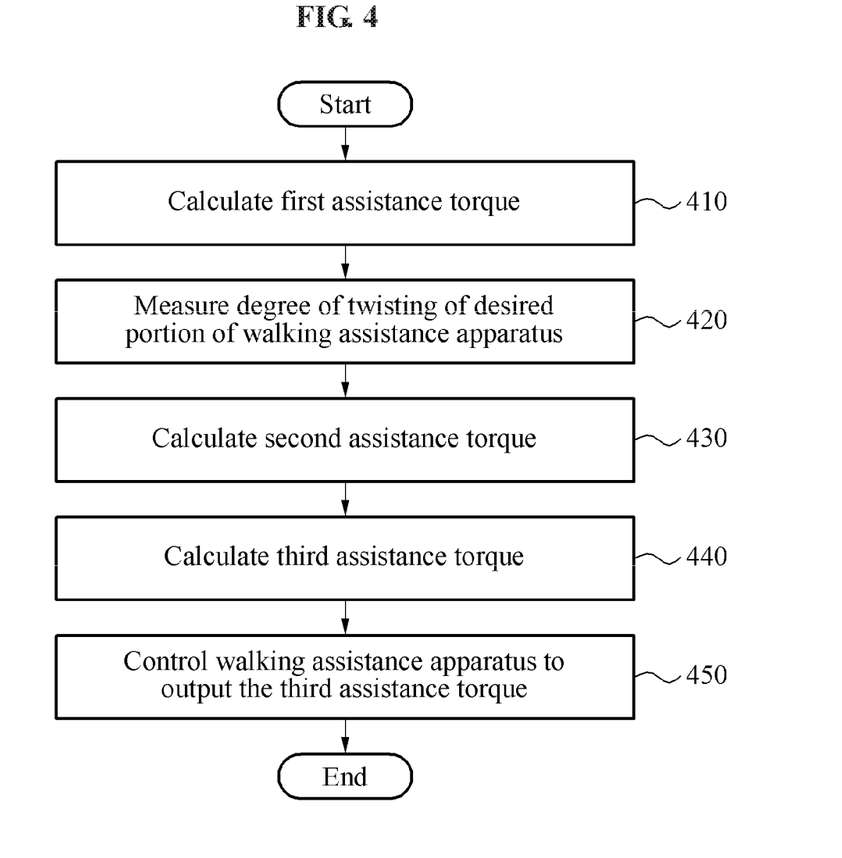
FIG. 4 is a flowchart illustrating an assistance torque calculation method according to at least one example embodiment.

FIG. 4 is a flowchart illustrating an assistance torque calculation method according to at least one example embodiment.

The assistance torque calculation method may be performed by a walking assistance apparatus through operations 410, 420, 430, and 440. A scheme by which the walking assistance apparatus outputs a calculated assistance torque will be described with reference to operation 450, and operation 450 may be additionally performed after operations 410 through 440.

Referring to FIG. 4, in operation 410, the processor 330 may calculate a first assistance torque to be provided to a user wearing the walking assistance apparatus 100. The first assistance torque may be, for example, an assistance torque regardless of a spring effect of a support frame.

The processor 330 may calculate the first assistance torque based on, for example, an operating state of the walking assistance apparatus 100. The operating state may be determined based on a movement of the user.

For example, the walking assistance apparatus 100 may measure an angle of a joint using a joint sensor attached to the driving portion 110. The joint may be, for example, at least one of a hip joint, a knee joint, and an ankle joint.

In this example, the processor 330 may analyze a movement of the user based on the measured angle of the joint. The processor 330 may determine the analyzed movement as one of a plurality of operating states that may be set in advance.

The processor 330 may calculate a first assistance torque corresponding to the movement of the user based on the determined operating state. For example, the processor 330 may calculate the first assistance torque corresponding to the movement of the user, based on a gait cycle corresponding to the determined operating state.

In operation 420, the bend sensor 320 may measure a degree of twisting of a desired portion (that may or may not be predetermined) of the walking assistance apparatus 100.

The desired portion (that may or may not be predetermined) of the walking assistance apparatus 100 may be, for example, a support frame. The support frame may be configured to support a waist. The desired portion (that may or may not be predetermined) of the walking assistance apparatus 100 will be further described with reference to FIG. 5.

When an external force is applied to the support frame of the walking assistance apparatus 100, a shape of the support frame may change. For example, when the support frame is formed of a carbon fiber and when an external force is applied to a portion of the support frame, the original shape of the support frame may change.

When the support frame is deformed, a magnitude of an assistance torque to be transferred may change. Due to a change in the magnitude of the assistance torque based on a deformation of the support frame, a degree to which the support frame is deformed may be measured and the magnitude of the assistance torque may be measured.

The bend sensor 320 may be attached to the desired portion (that may or may not be predetermined) of the walking assistance apparatus 100, and may measure the degree of twisting based on the twisting of the desired portion (that may or may not be predetermined).

The bend sensor 320 may include, for example, a flex sensor and an optical fiber Bragg grating sensor.

In operation 430, the processor 330 may calculate a second assistance torque transferred to the user, based on the measured degree of twisting.

The processor 330 may use a transformation function to calculate the second assistance torque. The transformation function may be, for example, a function to output the second assistance torque in response to an input of the degree of twisting.

The transformation function and a scheme of generating the transformation function will be further described with reference to FIGS. 6, 7, 8 and 9 below.

In operation 440, the processor 330 may calculate a third assistance torque based on the first assistance torque and the second assistance torque. For example, the third assistance torque may correspond to correction of a twisted support frame.

For example, the processor 330 may calculate a difference between the first assistance torque and the second assistance torque as the third assistance torque.

In operation 450, the processor 330 may control the walking assistance apparatus 100 to output the third assistance torque.

For example, the processor 330 may control the walking assistance apparatus 100 to provide a current corresponding to the third assistance torque to the driving portion 110 of the walking assistance apparatus 100.

The processor 330 may calculate a current value to generate the third assistance torque, based on a motor constant.

The processor 330 may control the third assistance torque to be output by driving the driving portion 110 based on the current value. The driving portion 110 may include a motor, for example.

Figure 5:
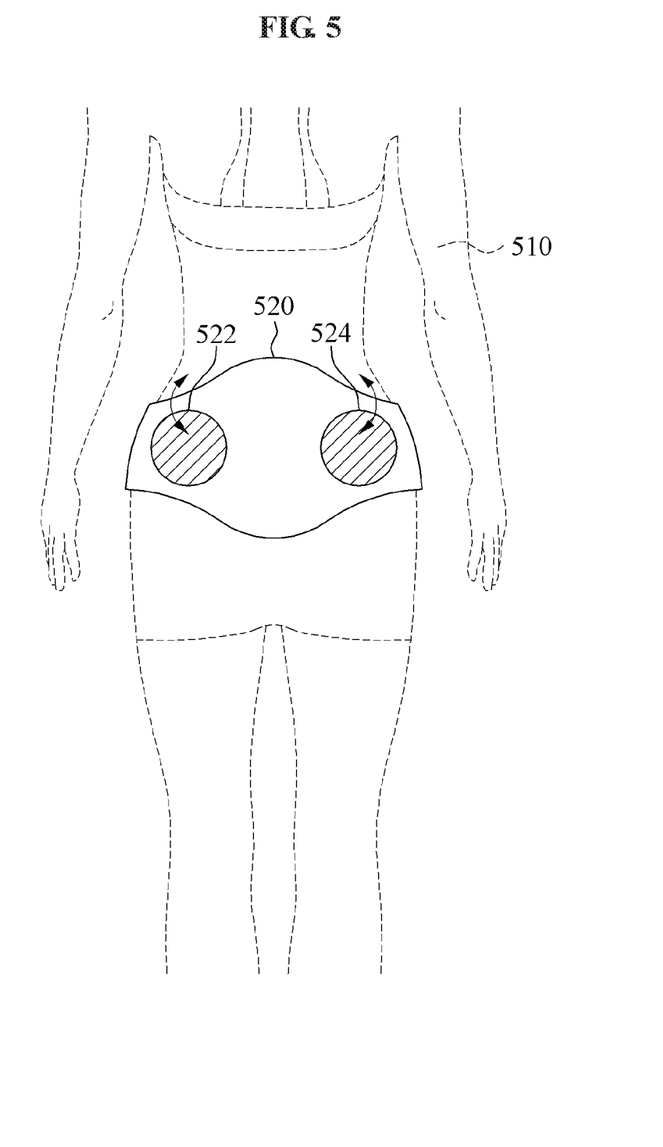
FIG. 5 illustrates an example of a twisted portion of a walking assistance apparatus according to at least one example embodiment.

FIG. 5 illustrates an example of a twisted portion of the walking assistance apparatus 100 according to at least one example embodiment.

A user 510 may wear the walking assistance apparatus 100. FIG. 5 illustrates a rear side of the user 510 wearing the walking assistance apparatus 100.

The walking assistance apparatus 100 may include a support frame 520. The support frame 520 may be worn around a waist of the user 510.

The support frame 520 may be implemented by various materials. For example, the support frame 520 may be implemented by a carbon fiber, however, there is no limitation thereto.

When an assistance torque is output by the driving portion 110, a shape of the support frame 520 may change due to the assistance torque. A first portion 522 and a second portion 524 of the support frame 520 may be greatly deformed compared to the other portions.

When a left motor outputs an assistance torque, the first portion 522 may be twisted by the assistance torque. When a right motor outputs an assistance torque, the second portion 524 may be twisted by the assistance torque.

When the left motor outputs the assistance torque, both the first portion 522 and the second portion 524 may be twisted. When the first portion 522 is twisted inwards, the second portion 524 may be twisted outwards based on the twisted first portion 522.

The bend sensor 320 may be attached to a desired portion (that may or may not be predetermined) of the support frame 520, and may measure a degree to which the desired portion (that may or may not be predetermined) is twisted. The desired portion (that may or may not be predetermined) may be, for example, at least one of the first portion 522 and the second portion 524.

Figure 6:
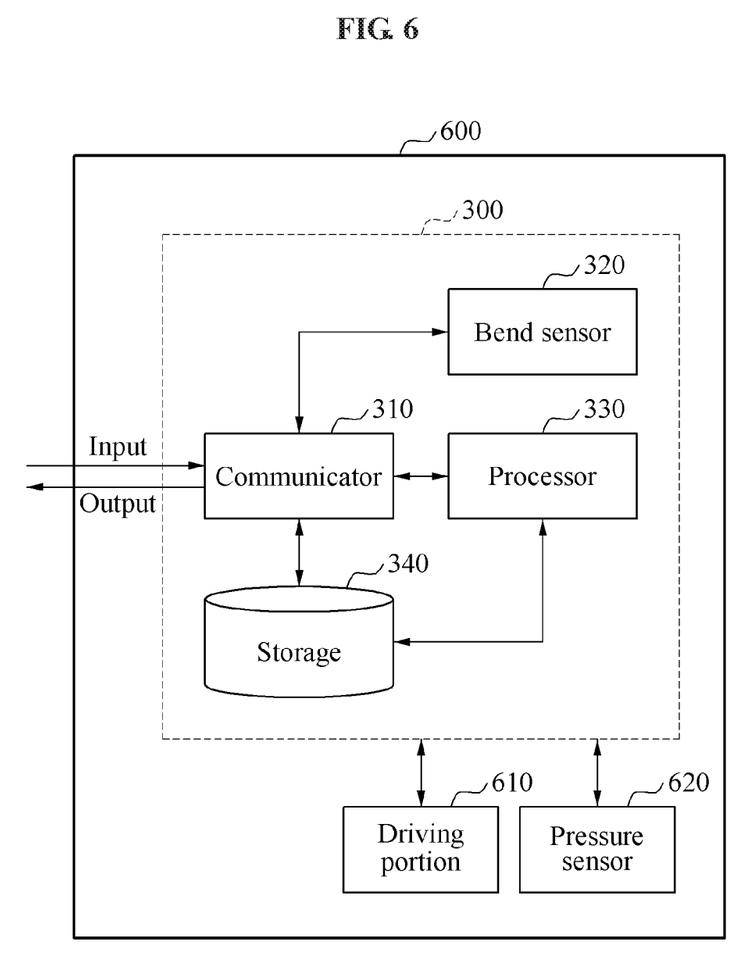
FIG. 6 illustrates a configuration of a walking assistance apparatus according to at least one example embodiment.

FIG. 6 illustrates a configuration of a walking assistance apparatus 600 according to at least one example embodiment.

Referring to FIG. 6, the walking assistance apparatus 600 may include the assistance torque calculation apparatus 300, a driving portion 610, and a pressure sensor 620. The assistance torque calculation apparatus 300, the driving portion 610, and the pressure sensor 620 are included in walking assistance apparatus 600 as shown in FIG. 6, however, the walking assistance apparatus 600 may further include other devices and the configuration is not limited to that of FIG. 6.

The driving portion 610 may correspond to, for example, the above-described driving portion 110.

Hereinafter, the driving portion 610 and the pressure sensor 620 will be further described with reference to FIGS. 7 and 8.

Figure 7:
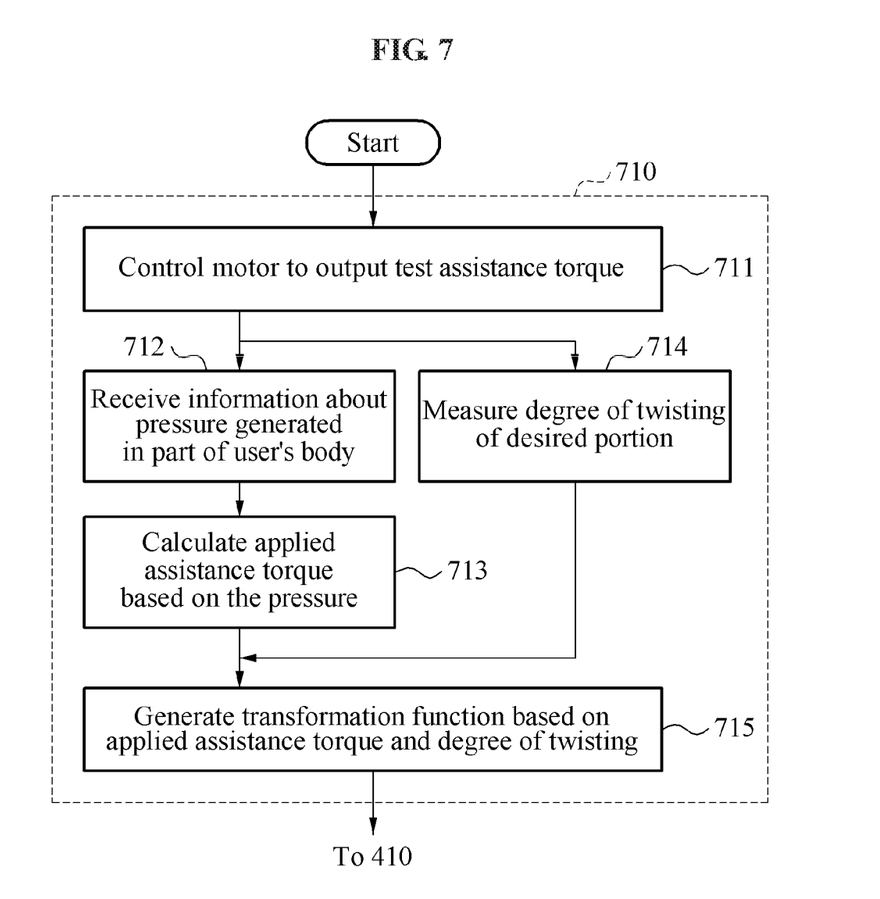
FIG. 7 is a flowchart illustrating an example of a scheme of generating a transformation function according to at least one example embodiment.

FIG. 7 is a flowchart illustrating an example of a scheme of generating a transformation function according to at least one example embodiment.

The transformation function used in operation 430 of FIG. 4 may be generated in advance before operation 410 is performed. In other words, operation 710 of generating a transformation function may be performed prior to operation 410.

Operation 710 may include operations 711 through 715.

In operation 711, the processor 330 may generate a test assistance torque. The test assistance torque may be used to measure an applied assistance torque and may have an arbitrary magnitude within a desired range. The applied assistance torque may be an assistance torque actually transferred to a user.

The processor 330 may control the driving portion 610 to output the test assistance torque. The driving portion 610 may include a motor.

In operation 712, the processor 330 may receive information about a pressure generated in a part of a user's body by the test assistance torque. The part of the body may be, for example, a thigh.

The generated pressure may be measured by the pressure sensor 620. The pressure sensor 620 may generate information about the measured pressure. The pressure sensor 620 will be further described with reference to FIG. 8 below.

The pressure sensor 620 and the communicator 310 may be connected to each other. For example, the pressure sensor 620 and the communicator 310 may be connected to each other using a wired communication scheme. In another example, the pressure sensor 620 and the communicator 310 may be connected to each other using a local area wireless network scheme.

The processor 330 may receive the information about the pressure from the pressure sensor 620 via the communicator 310.

In operation 713, the processor 330 may calculate the applied assistance torque based on the pressure.

For example, the processor 330 may calculate the applied assistance torque based on the measured pressure and a distance between a hip joint and a part of the body.

In operation 714, the bend sensor 320 may measure a degree of twisting of a desired portion (that may or may not be predetermined) of the walking assistance apparatus 600 twisted by the test assistance torque.

Operations 712, 713, and 714 may be performed in parallel.

Operations 711 through 714 may be repeatedly performed. When operations 711 through 714 are repeatedly performed, a relationship between a plurality of applied assistance torques and a plurality of degrees of twisting may be acquired. Information on the relationship may be stored in the storage 340.

In operation 715, the processor 330 may generate a transformation function based on the applied assistance torque and the degree of twisting.

In an example, the processor 330 may generate a transformation function based on the relationship. The transformation function may be, for example, a cubic function or a quartic function. In another example, the processor 330 may generate a transformation function using spline fitting.

Operation 710 may be performed for each of a left driving portion 610 and a right driving portion 610. For example, a transformation function for the left driving portion 610 and a transformation function for the right driving portion 610 may be generated.

As described above, operation 710 may be performed under assumption that the test assistance torque is generated by the left driving portion 610 and does not have an influence on a right thigh and the second portion 524.

In an example, the test assistance torque generated by the left driving portion 610 may have an influence on the right thigh and the second portion 524. For example, cross-coupling may occur.

In this example, a pressure generated in the right thigh by the test assistance torque generated by the left driving portion 610 may be measured in operation 712, and an applied assistance torque provided to the right thigh may be additionally calculated based on the pressure in operation 713. Also, a degree to which the second portion 524 is twisted by the test assistance torque may be measured in operation 714. In operation 715, the processor 330 may generate the transformation function for the left driving portion 610 based on an applied assistance torque provided to a left thigh, a degree of twisting of the first portion 522, the applied assistance torque provided to the right thigh, and the degree of twisting of the second portion 524.

The transformation function for the right driving portion 610 may be generated similarly to the generating of the transformation function for the left driving portion 610.

FIG. 8 illustrates an example of a position in which a pressure sensor is attached according to at least one example embodiment.

In an example, when the driving portion 610 outputs a test assistance torque in a direction in which an angle between a waist and legs increases, an applied assistance torque may be provided to a thigh through a connection portion 810 connected to the driving portion 610. In this example, a pressure sensor 830 may be located between an upper portion of the thigh and a thigh support 820.

In another example, when the driving portion 610 outputs a test assistance torque in a direction in which the angle between the waist and legs decreases, the pressure sensor 830 may be located between a lower portion of the thigh and the thigh support 820.

FIG. 9 illustrates a graph of a transformation function according to at least one example embodiment.

Points 911, 912, and 913 may be generated by repeatedly performing operations 711 through 714 of FIG. 7.

The processor 330 may generate a transformation function 920 based on the points 911 through 913.

In the above-described operation 430 of FIG. 4, the processor 330 may indirectly acquire a second assistance torque corresponding to the degree of twisting using the transformation function 920.

The units and/or modules described herein may be implemented using hardware components, software components, or a combination thereof. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

Algorithms for implementation or control of the walking assistance technologies discussed in this application may be used for implementation or control of more general purpose apparatuses and/or methods of controlling apparatuses.

Methods for implementation or control of the walking assistance technologies discussed in this application may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' may be interpreted as software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processes.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiments, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to walking assistance technologies, those skilled in the art will appreciate that some example embodiments may be applied to other types of systems, such as systems not used in the medical field (e.g., aerospace teleoperation systems, apparatuses for handling hazardous materials, patrol apparatuses, military apparatuses), humanoid apparatuses, or more general purpose control systems. Those skilled in the art will appreciate that the walking assistance technologies described in this application have a myriad of practical uses.

Although some example embodiments of the present disclosure have been shown and described, it would be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. An assistance torque calculation method, comprising:
    calculating a first assistance torque to be provided to a user wearing a walking assistance apparatus;
    measuring a degree of twisting of a supporting frame of the walking assistance apparatus;
    calculating a second assistance torque transferred to the user based on the degree of twisting; and
    calculating a third assistance torque based on the first assistance torque and the second assistance torque, the third assistance torque corresponding to correction of the twisting,
    wherein the calculating a second assistance torque comprises calculating the second assistance torque using a transformation function.

2. The assistance torque calculation method of claim 1, wherein the measuring a degree of twisting comprises measuring the degree of twisting using a bend sensor attached to the supporting frame of the walking assistance apparatus.

3. The assistance torque calculation method of claim 2, wherein the bend sensor comprises at least one of a flex sensor or an optical fiber Bragg grating sensor.

4. The assistance torque calculation method of claim 1, wherein the calculating a third assistance torque comprises calculating a difference between the first assistance torque and the second assistance torque as the third assistance torque.

5. The assistance torque calculation method of claim 1, further comprising:
    controlling the walking assistance apparatus to output the third assistance torque.

6. The assistance torque calculation method of claim 5, wherein the controlling the walking assistance apparatus comprises:
    calculating a current value to generate the third assistance torque, based on a motor constant; and
    outputting the third assistance torque by driving a motor based on the current value.

7. The assistance torque calculation method of claim 1, further comprising:
    generating the transformation function, prior to the calculating of the first assistance torque,
    wherein the transformation function is used to match the degree of twisting to the second assistance torque.

8. The assistance torque calculation method of claim 7, wherein the generating the transformation function comprises:
    controlling a motor to output a test assistance torque;
    receiving information about a pressure generated in a part of a body of the user by the test assistance torque;
    calculating an applied assistance torque based on the pressure;
    measuring the degree of twisting of the supporting frame of the walking assistance apparatus twisted by the test assistance torque; and generating the transformation function based on the degree of twisting and the applied assistance torque.

9. The assistance torque calculation method of claim 8, wherein the information about the pressure is generated by a pressure sensor.

10. The assistance torque calculation method of claim 8, wherein the part of the body is a thigh.

11. The assistance torque calculation method of claim 1, wherein the calculating a first assistance torque comprises calculating the first assistance torque based on an operating state of the walking assistance apparatus.

12. The assistance torque calculation method of claim 11, further comprising:
determining the operating state based on movement of the user.

13. The assistance torque calculation method of claim 1, wherein the supporting frame is a portion supporting a waist of the user.

14. An assistance torque calculation apparatus, comprising:
a bend sensor configured to measure a degree of twisting of a supporting frame of a walking assistance apparatus; and
a processor configured to,
calculate a first assistance torque to be provided to a user wearing the walking assistance apparatus,
calculate a second assistance torque transferred to the user based on the degree of twisting, and
calculate a third assistance torque based on the first assistance torque and the second assistance torque, the third assistance torque corresponding to correction of the twisting,
wherein the processor is further configured to calculate the second assistance torque using a transformation function.

15. The assistance torque calculation apparatus of claim 14, wherein the bend sensor comprises at least one of a flex sensor or an optical fiber Bragg grating sensor.

16. The assistance torque calculation apparatus of claim 14, wherein the processor is further configured to control a driving portion of the walking assistance apparatus to output a test assistance torque, receive information about a pressure generated in a part of a body of the user by the test assistance torque, and calculate an applied assistance torque based on the pressure,
wherein the bend sensor is further configured to measure the degree of twisting of the supporting frame of the walking assistance apparatus twisted by the test assistance torque, and
wherein the processor is further configured to generate the transformation function based on the degree of twisting and the applied assistance torque.

17. The assistance torque calculation apparatus of claim 16, wherein the part of the body is a thigh.

* * * * *